United States Patent [19]

Booth

[11] Patent Number: 4,482,748

[45] Date of Patent: * Nov. 13, 1984

[54] HYDROCARBONYLATION

[75] Inventor: Frank B. Booth, Placentia, Calif.

[73] Assignee: Celanese Corporation, New York, N.Y.

[*] Notice: The portion of the term of this patent subsequent to Jun. 22, 1993 has been disclaimed.

[21] Appl. No.: 926,046

[22] Filed: Jul. 19, 1978

Related U.S. Application Data

[63] Continuation of Ser. No. 464,657, Apr. 26, 1974, abandoned, which is a continuation of Ser. No. 81,502, Oct. 16, 1970, abandoned, which is a continuation of Ser. No. 642,191, May 29, 1967, abandoned.

[51] Int. Cl.$^3$ ............................................. C07C 45/50
[52] U.S. Cl. .................................... 568/454; 568/429; 568/444; 564/305; 260/598; 260/599; 260/578; 260/584 A; 260/602; 260/600
[58] Field of Search ................... 260/604 HF; 568/454

[56] References Cited

U.S. PATENT DOCUMENTS

| | | | |
|---|---|---|---|
| 2,694,735 | 11/1954 | Hull et al. | 260/604 HF |
| 2,828,344 | 3/1958 | Hughes et al. | 260/604 HF |
| 3,102,899 | 9/1963 | Cannell | 260/439 |
| 3,167,555 | 1/1965 | Farkas et al. | 260/268 |
| 3,168,553 | 2/1965 | Slaugh | 260/497 |
| 3,239,566 | 3/1966 | Slaugh et al. | 260/604 HF |
| 3,239,570 | 3/1966 | Slaugh et al. | 260/632 HF |
| 3,278,612 | 10/1966 | Greene | 260/632 HF |
| 3,351,666 | 11/1967 | Mertzweiller et al. | 260/604 HF |
| 3,458,547 | 7/1969 | Coffey | 260/604 HF X |
| 3,480,659 | 11/1969 | Dewhirst | 260/465.1 |
| 3,487,112 | 12/1969 | Paulik et al. | 260/604 HF |
| 3,499,932 | 3/1970 | Pruett et al. | 260/598 |
| 3,499,933 | 3/1970 | Pruett et al. | 260/598 |
| 3,511,880 | 5/1970 | Booth | 260/604 HF |
| 3,515,757 | 6/1970 | Sibert | 260/604 HF |
| 3,527,809 | 9/1970 | Pruett et al. | 260/604 HF |
| 3,594,425 | 7/1971 | Brader et al. | 260/604 HF |
| 3,965,192 | 6/1976 | Booth | 260/598 |
| 4,108,905 | 8/1978 | Wilkinson | 260/604 HF |
| 4,110,404 | 8/1978 | Schaeffer et al. | 260/604 HF |

FOREIGN PATENT DOCUMENTS

| | | |
|---|---|---|
| 1530136 | 5/1968 | France . |
| 40-22735 | 7/1965 | Japan . |
| 665705 | 1/1952 | United Kingdom . |
| 988941 | 4/1965 | United Kingdom . |

OTHER PUBLICATIONS

Jardine et al., Chemistry and Industry, (England), Communications to the Editor, 3/27/65, p. 560.
Osborn et al., Chemical Communications, No. 2, (1/27/65), p. 17.
Alfa, Journal of Organometallic Chemistry, vol. 7, No. 3, (1967), back of outside cover.
Hallman et al., Chemical Communications, (No. 7/1967), pp. 305-306.

Primary Examiner—Bernard Helfin
Attorney, Agent, or Firm—Kenneth A. Genoni

[57] ABSTRACT

The homogeneous catalysis of the hydrocarbonylation of olefins using a catalyst comprising a complex between an organic ligand and a Group VIII noble metal hydride carbonyl. The reaction is performed at mild conditions including temperatures from 50°-200° C. and pressures from 1 to 10,000 atmospheres to produce a predominantly aldehyde product having a high normal to iso distribution. The aldehyde products so produced are useful as intermediates for hydrogenation to aliphatic alcohols, for aldol condensation to produce plasticizers, for oxidation to produce aliphatic acids, etc.

4 Claims, No Drawings

HYDROCARBONYLATION

This is a continuation of application Ser. No. 81,502, filed Apr. 26, 1974 which is a continuation of application Ser. No. 81,502 filed Oct. 16, 1970, which is a continuation of application Ser. No. 642,191, filed May 29, 1967, all now abandoned.

DESCRIPTION OF THE INVENTION

The invention relates to the reductive carbonylation of olefins to aliphatic aldehydes having a high ratio of normal to iso distribution. The invention comprises the use of a hydride of a Group VIII noble metal carbonyl catalyst that is complexed with an organic ligand selected from the class consisting of organic phosphines, arsines and stibines. When the catalyst is employed as a hydride in accordance with this invention, a high activity is observed and, surprisingly, it was found that the hydride does not promote undesired reactions such as reduction of the desired carbonyl product.

While it has been proposed by previous investigators—*Chemical Communications,* January 1965, page 17—that complexes of triphenylphosphine and rhodium halides be employed as carbonylation catalysts, these reactions have previously been dependent to a substantial degree on the nature of the solvent employed. In addition, it has been necessary to perform the reaction at relatively mild conditions to preclude any substantial degree of hydrogenation activity or the catalyst in the preparation of the carbonyl products. In copending applications, Ser. Nos. 581,562 filed Jan. 4, 1966 and 579,825 filed Sept. 16, 1966, it is disclosed that the activity of these noble metal salt catalysts can be enhanced by the inclusion of cocatalysts in the liquid phase such as heterocyclic bridgehead amines or strongly basic materials.

I have now found that the activity of a catalyst containing a complex of an organic ligand and a Group VIII noble metal carbonyl can be greatly enhanced if the catalyst is employed as a hydride rather than as the metal or as a salt, as heretofore employed. It is therefore my invention to employ in the hydrocarbonylation of alpha olefins a catalyst comprising a complex between an organic biphyllic ligand and a Group VIII noble metal hydride carbonyl.

The catalyst comprises a complex combination of a Group VIII noble metal hydride with carbon monoxide and an organic ligand. The Group VIII noble metal can be of the palladium subgroup, i.e., palladium, rhodium or ruthenium, or of the platinum subgroup, i.e., platinum, osmium or iridium. The catalyst is employed in its hydride form and can be prepared by treatment of the metal salt with a strong reducing agent as set forth hereinafter. The metal hydride carbonyl is in association with a biphyllic ligand which is an organic material having one atom selected from the group of phosphorus, arsenic, antimony and bismuth in the trivalent state and having an unshared pair of electrons capable of coordinate covalent bonding with the catalyst to thereby form a complex useful in the catalysis.

With the aforementioned catalyst, described in greater detail hereinafter, the carbonylation of ethylenically unsaturated compounds proceeds rapidly at relatively mild conditions including temperatures from about 0° to about 250° C. and pressures of from 1 to about 1000 atmospheres with ratios of hydrogen to carbon monoxide in the reactants from 10:1 to about 1:10.

The ethylenically unsaturated compound carbonylated in accordance with my invention can comprise any olefin having from 2 to about 25 carbons; preferably from 2 to about 18 carbons. This olefin has the following structure:

wherein $R_1$, $R_2$, $R_3$ and $R_4$ are hydrogen, alkyl, cycloalkyl, aryl, alkaryl, aralkyl, hydroxyalkyl, hydroxyaryl, aminoalkyl or aminoaryl or wherein one of said $R_1$ and $R_2$ and one of said $R_3$ and $R_4$ together form a single alkylene group having from 2 to about 8 carbons.

Examples of useful olefins are the hydrocarbon olefins such as ethylene, propylene, butene-1, butene-2, 2-methylbutene-1, cyclobutene, hexene-1, hexene-2, -cyclohexene, 3-ethylhexene-1, isobutylene, octene-1, 2-propylhexene-1, ethylcyclohexene, decene-1, cycloheptene, cyclooctene, cyclononene, 4,4'-dimethylnonene-1, dodecene-1, undecene-3, 6-propyldecene-1, tetradecene-2, 7-amyldecene-1, oligomers of olefins such as propylene tetramer, ethylene trimer, etc., hexadecene-1, 4-ethyltridecene-1, octadecene-1, 5,5-dipropyldodecene-1, vinylcyclohexane, allylcyclohexane, styrene, p-methylstyrene, alpha-methylstyrene, p-vinylcumene, beta-vinylnaphthalene, 1,1-diphenylethylene, allylbenzene, 6-phenylhexene-1, 1,3-diphenylbutene-1, 3-benzylheptene-1, o-vinyl-p-xylene, m-aminostyrene, divinylbenzene, 1-allyl-4-vinylbenzene, allylamine, p-aminostyrene, allylaniline, crotonyl alcohol, allylcarbinol, beta-allylethanol, allylphenol, etc. Of the preceding the alpha olefins and olefins having 2 to about 8 carbons are preferred classes.

The reactionis performed under liquid phase conditions and, when the olefin comprises a liquid at the reaction conditions, the olefin can be used in excess to provide the liquid reaction medium. If desired, however, any suitable organic liquid can be employed as a reaction solvent; preferably, organic solvents which are inert to the reaction conditions, the reactants, the catalyst and the products are employed. Examples of suitable solvents which can be used in accordance with my invention include hydrocarbons such as the aromatic, aliphatic or alicyclic hydrocarbons, ethers, esters, ketones, etc.

Examples of suitable hydrocarbons that can be employed in the solvents include aromatic hydrocarbons such as benzene, toluene, xylene, ethylbenzene, tetralin, etc.; aliphatic hydrocarbons such as butane, pentane, isopentane, hexane, isohexane, heptane, octane, isooctane, naphtha, gasoline, kerosene, mineral oil, etc.; alicyclic hydrocarbons, e.g., cyclopentana, cyclohexane, methylcyclopentane, decalin, indane, etc.

Various alkyl and aryl ketones can also be employed as the reaction solvent, e.g., acetone, methylethyl ketone, diethyl ketone, diisopropyl ketone, ethyl-n-butyl ketone, methyl-n-amyl ketone, cyclohexanone, diisobutyl ketone, etc.

Ethers can also be employed as the reaction solvent, e.g., diisopropyl ether, di-n-butyl ether, ethylene glycol diisobutyl ether, methyl o-tolyl ether, ethylene glycol dibutyl ether, diisoamyl ether, methyl p-tolyl ether, methyl m-tolyl ether, dichloroethyl ether, ethylene glycol diisoamyl ether, diethylene glycol diethyl ether, ethylbenzyl ether, diethylene glycol diethyl ether, diethylene glycol dimethyl ether, ethylene glycol dibutyl ether, ethylene glycol diphenyl ether, triethylene glycol diethyl ether, diethylene glycol di-n-hexyl ether, tetraethylene glycol dimethyl ether, tetraethylene glycol dibutyl ether, et.

Various esters can also be employed as the solvent, e.g., ethyl formate, methyl acetate, ethyl acetate, n-propyl formate, isopropyl acetate, ethyl propionate, n-propyl acetate, sec-butyl acetate, isobutyl acetate, ethyl n-butyrate, n-butyl acetate, isoamyl acetate, n-amyl acetate, ethyl formate, ethylene glycol diasetate, glycol diformate, cyclohexyl acetate, furfuryl acetate, isoamyl n-butyrate, diethyl oxalate, isoamyl isovalerate, methyl benzoate, diethyl malenate, valerolactone, ethyl benzoate, methyl salicylate, n-propyl benzoate, n-dibutyl oxalate, n-butyl benzoate, diisoamyl phthalate, dimethyl phthalate, diethyl phthalate, benzyl benzoate, n-dibutyl phthalate, etc. A preferred class of ester solvents includes the lactones, e.g., butyralactone, valerolactone and their derivatives having lower ($C_1$-$C_5$) alkyl substituents.

Alcohols can also be employed as a reaction solvent. Preferably tertiary alcohols are employed since these materials are substantially non-reactive under the reaction conditions. Primary and secondary alcohols can be employed but are less preferred since these materials can react with aldehyde compounds under the reaction conditions to produce acetals. While in some instances these may be desired products, it is generally desirable to produce the carbonyl compound or alcohol directly without the formation of the acetal. It is of course apparent, if desired, that the acetal can be hydrolyzed to obtain the aldehyde. Examples of alcohols that can be employed as solvents include the aliphatic and alicyclic alcohols such as methanol, ethanol, isopropanol, butanol, t-butanol, t-amyl alcohol, hexanol, cyclohexanol, etc.

The catalyst comprises a Group VIII noble metal hydride in complex association with carbon monoxide and a biphyllic ligand. The biphyllic ligand is a compound having at least one atom with a pair of electrons capable of forming a coordinate covalent bond with a metal atom and simultaneously having the ability to accept the electron from the metal, thereby imparting additional stability to the resulting complex. Biphyllic ligands can comprise organic compounds having at least about 3 carbons and containing arsenic, antimony, phosphorus or bismuth in a trivalent state. Of these the phosphorus compounds, i.e., the phosphines, are preferred; however, the arsines, stibines and bismuthines can also be employed. In general these biphyllic ligands have the following structure:

or the following structure:

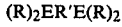

wherein E is a trivalent atom selected from the class consisting of phosphorus, arsenic, antimony and bismuth;
wherein R is a member of the class consisting of hydrogen, alkyl from 1 to 8 carbon atoms, aryl from 6 to 8 carbons and amino, halo and alkoxy substitution products thereof; and
wherein R' is alkylene having from 1 to about 8 carbons.

Examples of suitable biphyllic ligands having the aforementioned structure and useful in my invention to stabilize the catalyst composition are the following: trimethylphosphine, triethylarsine, triethylbismuthine, triisopropylstibine, chlorodiethylphosphine, triaminobutylarsine, ethyldiisopropylstibine, tricyclohexylphosphine, triphenylphosphine, triphenylbismuthine, tri(o-toly)phosphine, phenyldiisopropylphosphine, phenyldiamylphosphine, ethyldiphenylphosphine, chlorodixylylphosphine, chlorodiphenylphosphine, tris(diethylaminomethyl)phosphine, ethylene bis(diphenylphosphine), hexamethylene bis(diisopropylarsine), pentamethylene bis(diethylstibine), diphenyl(N,N-dimethylanilinyl)phosphine, trianilinylphosphine, tri(3,5-diaminophenyl)phosphine, trianilinylarsine, anilinyldiphenylbismuthine, etc. Of the aforementioned, the arylphosphines are preferred because of the demonstrated non-equivalent greater activity of catalysts comprising the arylphosphines.

The reaction is performed under relatively mild conditions including temperatures from about 50° to about 200° C.; preferably from about 70° to about 180° C. Sufficient pressure is used to maintain the reaction medium in liquid phase. Although atmospheric pressure can be used, the rate of reaction is increased by superatmospheric pressures and, therefore, pressures from about 5 to about 300 atmospheres and preferably from about 10 to about 100 atmospheres are used. The ratio of the reactants can be widely varied if desired, e.g., the molecular ratio of hydrogen to carbon monoxide can be varied from about 1:10 to about 10:1. The preceding conditions are maintained by conventional means. Since the reaction is exothermic, the temperature can be maintained by suitable cooling of all or a portion of the reaction zone contents. The pressure can be maintained by the pressure of the gases supplied to the reaction zone. If desired, a suitable inert gas can also be charged to the reaction zone to reduce the partial pressures of the reacted gases, i.e., hydrogen and carbon monoxide. Nitrogen is a suitable inert gas.

The relative concentration of the carbon monoxide and hydrogen affects the distribution of the normal and branched chain isomers in the product. The carbon monoxide to hydrogen ratio can be maintained from about 1:10 to about 1:3 and preferably from about 1:10 to about 1:5 to favor production of the straight chain aldehyde. Surprisingly, under high hydrogen partial pressures and, even in the presence of a noble metal hydride, the straight chain product can be obtained in amounts from 2 to 8 times the yield of the branched chain aldehyde.

The Group VIII noble metal hydride complex with carbon monoxide and the organic ligand can be formed by reduction of a metal salt carbonyl-ligand complex or can be formed from the metal hydrides themselves. Some of the Group VIII noble metal hydride carbonyls are commercially available and can be purchased and used directly. Examples of suitable sources of the noble metals are as follows: bis(triphenylphosphine)iridium carbonyl chloride; tris(triphenylphosphine)iridium carbonyl hydride; iridium carbonyl; iridium tetrabromide; iridium tribromide; iridium trifluoride; iridium trichloride; osmium trichloride; chloroosmic acid; palladium hydride; palladous chloride, palladous cyanide; palladous iodide; palladous nitrate; platanic acid; platanous iodide; palladium cyanide; sodium hexachloroplatinate; potassium trichloro(ethylene)platinate(II); chloropentaamminorhodium(III) chloride; rhodium dicarbonyl chloride dimer; rhodium nitrate; rhodium trichloride; tris(triphenylphosphine)rhodium carbonyl hydride;

tris(triphenylphosphine)rhodium(I)chloride; ruthenium trichloride; tetraamminorutheniumhydroxychloro chloride; etc.

Of the aforementioned, the hydride carbonyl complexes with triphenylphosphine of rhodium and iridium can of course be directly added to the reaction as the catalytically active material. The hydride carbonyls can also be formed from the hydrides such as palladium hydride by adding the palladium hydride and excess of the organic ligand to a reaction zone containing an inert liquid and introducing carbon monoxide into the liquid phase to form the carbonyl. Atmospheric or superatmospheric pressures up to about 1000 atmospheres can be used as desired to accelerate the formation of the carbonyl complex catalyst.

The catalyst can also be formed from the Group VIII noble metal salts previously mentioned. In this preparation the Group VIII noble metal salt is subjected to a reduction with a strong reducing agent and this reduction can be performed before or after forming of the complex catalyst with carbon monoxide and the organic ligand. Suitable strong reducing agents comprise the alkali metal hydrides and the alkali metal boron and aluminum hydrides such as sodium hydride, potassium hydride, lithium hydride, boron hydride, e.g., sodium borohydride, potassium borohydride, lithium borohydride, cesium borohydride, sodium aluminum hydride, lithium aluminum hydride, potassium aluminum hydride, cesium aluminum hydride, etc., in a suitable inert organic solvent such as any of those aforementioned. The aforementioned reducing agents are preferred when a halide salt is the source of the Group VIII noble metal. When non-halide sources are used such as the nitrate or sulfate, salts are used, reduction to the hydride can be achieved by treatment with hydrazine using any inert organic solvent such as those aforementioned. The reduction is performed at relatively mild temperatures from about 25° to about 75° C. and, preferably, is performed in aqueous alkanol solvent. The reduction results in the reduction of the metal salt, e.g., rhodium chloride, to rhodium hydride. When this reaction is performed in the presence of the organic ligand and under carbon monoxide pressure, the Group VIII noble metal hydride complex with carbon monoxide and triphenylphosphine can be obtained directly.

The catalyst can be formed in the reaction zone prior to introducing the olefin and commencing the hydrocarbonylation or it can be purified by crystallization from the liquid media used in their preparation. These hydride catalysts have characteristic melting points and have a characteristic deflection in the infrared spectra, e.g., the stretching frequency of the rhodium hydride bond appears at 2020 cm$^{-1}$.

The hydrocarbonylation reaction is performed under relatively mild conditions including temperatures from about 50° to about 200° C.; preferably from about 70° to about 150° C. The reaction is initiated by charging the noble metal hydride as such or as the preformed catalyst complexed with carbon monoxide and the organic ligand to the reaction zone and then introducing the reactants, i.e., the olefin, carbon monoxide and hydrogen. Sufficient pressure is used to maintain the reaction medium in liquid phase. Although atmospheric pressure can be used, the rate of reaction is increased by superatmospheric pressures and, therefore, pressures from about 5 to about 350 atmospheres and preferably from about 10 to about 100 atmospheres are used. The ratio of the reactants can be widely varied if desired, e.g., the molecular ratio of hydrogen to carbon monoxide can be varied from about 1:10 to 10:1.

The preceding reaction conditions are maintained by conventional means. Since the reaction is exothermic, the temperature can be maintained by suitable cooling of all or a portion of the reaction zone contents. The pressure can be maintained by the pressure of the gases supplied to the reaction zone. If desired, a suitable inert gas can also be charged to the reaction zone to reduce the partial pressures of the reacted gases, i.e., hydrogen and carbon monoxide. Nitrogen is a suitable inert gas.

The relative concentration of the carbon monoxide and hydrogen affects the distribution of the normal and branched chain isomers in the product. The carbon monoxide to hydrogen ratio can be maintained from about 1:10 to about 1:3 and preferably from about 1:10 to about 1:5 to favor production of the straight chain aldehyde. Surprisingly, under these high hydrogen partial pressures the straight chain product can be obtained in amounts from 2 to 8 times the yield of the branched chain aldehyde.

The process can be conducted continuously or batchwise; however, the continuous processing is preferred. In the latter preferred technique, the catalyst is charged to the reaction zone in a suitable solvent or in excess of the olefin and the gaseous reactants are introduced into contact with the reaction solvent and catalyst in the reaction zone. A continuous withdrawal of the liquid phase in the reaction zone can be employed; this material is then reduced in pressure to remove the dissolved gases which can be recycled, cooled and then distilled to recover the desired products. When low molecular weight products are produced, e.g., propionaldehyde, this product can be recovered by employing a high gas rate through the reactor to strip the product from the reaction solvent which, desirably, is a higher boiling liquid such as tertiary butanol, tertiary amyl alcohol, butyrolactone, etc.

Because the reaction conditions are very mild, the products can remain in the reaction zone without encountering undue degradation to less desired products or without experiencing any aldol condensation and, therefore, batchwise operation can be practiced by introducing the olefin, hydrogen and carbon monoxide into contact with the catalyst solution until a sufficient inventory of product is accumulated in the reaction zone and thereafter the reaction discontinued and the product recovered by suitable steps, typically distillation.

In the hydroformylation reaction, the preferred catalyst is rhodium hydride.

A preferred embodiment of the invention utilizes excess of the organic ligand. Use of excess amounts as hereafter defined has been found to increase the rate of reaction and to increase the yield of the normal, i.e., straight chain, carbonyl product. Excess quantities of the organic ligand include from 2 to about 100 times the stoichiometric amount of ligand that is complexed with the noble metal catalyst. Preferably the amount in excess is from 5 to about 20 times this stoichiometric quantity. The stoichiometric quantity varies between the noble metals but is from 2 to about 4 and usually 3 molar quantities of ligand per atomic quantity of noble metal.

The practice of the invention will now be illustrated by the following examples which will also serve to demonstrate the results obtainable thereby:

EXAMPLE 1

The rhodium hydride catalyst, $Rh(H)(CO)[(C_6H_5)_3P]_3$, was prepared in the following example wherein 0.5 gram of bis(triphenylphosphine)rhodium carbonyl chloride, $RhCl(CO)[(C_6H_5)_3P]_2$, and one gram of triphenylphosphine, $(C_6H_5)_3P$, were suspended in 50 milliliters of methanol and warmed to 55° C. To the suspension was then slowly added 50 milliliters of methanol containing 2 grams of sodium borohydride. The addition was complete within about 15 minutes and the suspension was then cooled and filtered and the separated solid was washed thoroughly with methanol and air dried. The recovered solid was a yellow, crystalline material having a melting point of 125° C. and a characteristic infrared spectra indicating the presence of the rhodium hydride.

The hydroformylation is practiced with the preceding catalyst by charging 0.5 gram of the tris(triphenylphosphine)rhodium carbonyl hydride and 500 milliliters toluene to a half gallon, stainless steel autoclave together with 120 grams propylene. The autoclave is pressured an increment of 300 psi with carbon monoxide and an additional 300 psi increment with hydrogen, then heated to 95° C. A pressure drop of 200 psi occurs over a period of eight minutes at 95° C. and the autoclave is cooled, vented and the liquid contents are weighed to determine a 59 gram weight increase. Analysis by gas chromatography revealed that the products are mixed butyraldehydes with a normal to iso ratio of 1.2.

The catalyst was also prepared from rhodium trichloride by the addition of one gram hydrated rhodium trichloride to 200 milliliters methanol and 20 milliliters water. To the mixture was added 7 grams of triphenylphosphine and the system was then refluxed for 30 minutes under an atmosphere containing equal molar quantities of carbon monoxide and hydrogen. Thereafter 2 grams of sodium borohydride dissolved in 50 milliliters of methanol were added and the system was refluxed for another 30 minutes, then cooled and filtered. The yellow solid was washed thoroughly with methanol and air dried to obtain 3.49 grams of tris(triphenylphosphinerhodium carbonyl hydride.

In a similar fashion, the complexes of the hydrides of the ruthenium and palladium members of the Group VIII noble metals can be formed by substitution of the 1.0 gram rhodium trichloride with 1.0 gram of ruthenium trichloride or 1.0 gram of palladous chloride in the preceding experiment.

A hydride catalyst is prepared by placing 300 milliliters methanol, 2 grams rhodium nitrate and 12 grams triphenylphosphine in a flask fitted with a reflux condenser. A carbon monoxide and hydrogen gas stream containing equal quantities of the gases was passed through the solution which was heated to reflux temperature and maintained at that temperature for 30 minutes. A solution of 2.0 milliliters of 85 weight percent hydrazine hydrate in 25 milliliters water was then added and refluxing continued for an additional 30 minutes. The flask contents were then cooled, filtered and the solid product was washed with methanol and air dried. A total of 4.4 grams of tris(triphenylphosphine)carbonyl rhodium hydride was recovered and identified by its decomposition point of 128° C. and characteristic infrared spectrum.

The hydroformylation is practiced with the preceding catalyst by charging 2.4 grams of the recovered solid, 3.5 grams triphenylphosphine and 2.0 grams 1,4-diazabicyclo(2.2.2)octane to a one-half gallon autoclave with 500 milliliters dimethyl ketone. The autoclave is charged with 105 grams propylene and carbon monoxide is added to provide a 300 psi increase in pressure and then hydrogen is added to provide another 300 psi increase. The autoclave is heated to 95° C. and maintained at that temperature for 10 minutes during which the pressure drops 300 psi. The autoclave is cooled, depressured and opened and the liquid products weighed to reveal a 73 gram weight increase. The products are identified by gas chromatography as mixed butyraldehydes with a normal to iso ratio of 2.0.

EXAMPLE 2

The use of the catalyst for the carbonylation is illustrated in the following example wherein 0.50 gram of the tris(triphenylphosphine) rhodium carbonyl hydride catalyst and 5 grams of triphenylphosphine are introduced into an autoclave containing 500 milliliters toluene. The autoclave is closed and 104 grams of propylene are introduced into the autoclave and the autoclave pressure is then raised an increment of 300 psi with carbon monoxide and then raised an additional 300 psig increment with introduction of hydrogen. The autoclave is then heated to 95° C. and a pressure drop of 110 psig occurs within 2 minutes. Upon completion of the reaction the autoclave is cooled, depressured, opened and the weight increase of the liquid contents measured to indicate a 45 gram increase. The products are analyzed by gas chromatoraphy to indicate substantially pure butyraldehyde having a ratio of normal to iso of 2.1.

The carbonylation can be repeated by substitution of the 0.50 gram tris(triphenylphosphine)carbonyl rhodium hydride with 0.50 gram tris(triphenylphosphine)carbonyl ruthenium hydride or 0.50 gram of tris(triphenylphosphine)palladium hydride, although a lesser degree of reactivity will be observed.

When the reaction is repeated in the presence of 2.0 grams of triethylene diamine, for a period of seven minutes, a pressure drop of 300 psi occurs and an 81 gram weight increase is obtained. The product comprises essentially pure butyraldehydes having a normal to iso ratio of 2.1.

When the reaction is repeated in the presence of 6.6 grams of tri-n-butylamine, a weight increase of 43 grams occurs in 3 minutes and the products produced are butyraldehydes with a normal to iso ratio of 2.1.

The reaction is repeated using 0.6 grams tris(triphenylphosphine)rhodium carbonyl chloride, 5 grams excess triphenylphosphine and 500 milliliters toluene which are introduced into the autoclave. Into the autoclave is then introduced 113 grams propylene and the autoclave is pressured an increment of 300 psig with carbon monoxide and then an additional increment of 300 psig with hydrogen. The autoclave is heated to 95° C. and a pressure drop of about 300 psig occurs over a 50 minute period. Upon completion of the reaction, the autoclave is cooled, depressured, opened and the contents are weighed to reveal a weight increase of 67 grams. The product is analyzed by gas chromatography to indicate that it is a mixture of normal and iso butyraldehydes having a ratio of normal to iso of 2.1.

The reaction was repeated using 0.6 gram bis(triphenylphosphine)rhodium carbonyl chloride, 5 grams of excess triphenylphosphine, 2 grams of triethylenediamine(1,2-diazabicyclo(2.2.2) octane, and 500 milliliters of toluene which are charged to the autoclave. Into the autoclave is then introduced 119 grams propylene and the autoclave is pressured to 300 psig with carbon monoxide and then an additional 300 psig with hydrogen. The autoclave is then heated to 95° C. and a pressure drop of 30 psig occurs within 7 minutes. The autoclave is cooled, depressured and opened and the liquid contents are weighed to reveal a total of 87 gram weight increase. The products are analyzed by gas chromatography to indicate that the product was substantially pure butyraldehyde having a normal to iso ratio of 2.

EXAMPLE 3

The process is applied to other olefins by charging 0.5 gram tris(triphenylphosphine)rhodium carbonyl hydride, 5.0 grams triphenylphosphine and 500 milliliters toluene to the autoclave. The autoclave is closed and 118 grams of cis and trans butene-2 are introduced and the autoclave is pressured an incremental 300 psi with carbon monoxide and an additional 300 psi with hydrogen. The autoclave is heated to 95° C. and maintained at that temperature for 90 minutes, then cooled, depressured and opened. The liquid contents are analyzed by gas chromatography to determine that 34 grams of 3-methylbutanal-4 and 3 grams of pentanal are formed.

The preceding experiment is repeated except the autoclave is heated to 150° C. and maintained at that temperature for 9 minutes. The liquid contents are analyzed to determine that 36 grams of 3-methylbutanal-4 and 12 grams of pentanal are formed.

The experiment is repeated charging 100 grams of octene-1. The autoclave is heated to 95° C. and maintained at that temperature for 7 minutes during which time a pressure drop of 140 psi occurs. The liquid contents of the autoclave are analyzed to reveal that 61 grams of nonylaldehydes are formed having a normal to iso ratio of about 3 to 1.

The preceding experiment is repeated by charging 101 grams isobutylene to the autoclave. The autoclave is heated to 95° C. and a 20 psi pressure drop is observed within 18 minutes. The autoclave is then heated to 155° C. and maintained at that temperature for 20 minutes and a pressure drop of 140 psi occurs. The liquid products are weighed to determine that a 48 gram weight increase occurred and the product is found to be isoamylaldehyde.

EXAMPLE 4

The hydride iridium catalyst is prepared by the addition of 1.0 gram iridium chloride, 6.0 grams triphenylphosphine and 250 milliliters of N,N'-dimethylformamide to a flask fitted with a reflux condenser. The flask contents are refluxed for 3 hours while passing a gas comprising equal volumes of carbon monoxide and hydrogen through the liquid. Then 50 milliliters of a methanol solution containing 2.0 grams sodium borohydride is added and the flask contents are maintained at reflux for 30 minutes. The flask is then cooled and its contents filtered to recover 0.55 gram of tris(triphenylphosphine)carbonyl iridium hydride identified by its characteristic infrared spectrum.

A one-half gallon, stainless steel autoclave is charged with 0.5 gram of the tris(triphenylphosphine)carbonyl iridium hydride, 5.0 grams triphenylphosphine and 500 milliliters toluene. The autoclave is closed and 110 grams propylene is added; carbon monoxide is added to provide 300 psi incremental pressure increase and hydrogen is then added to provide another 300 psi incremental increase in pressure. The autoclave is heated to 150° C. and maintained at that temperature for 35 minutes while the pressure is observed to drop 80 psi. The autoclave is then cooled, depressured and opened and the liquid products weighed to indicate a 20 gram weight increase. The product identified by gas chromatography was butyraldehyde with a normal to iso ratio of 1.2 to 1.0.

The carbonylation can be similarly practiced with the complexes of the hydrides of the osmium and platinum members of the Group VIII noble metals by substitution of the 0.5 gram tris(triphenylphosphine)carbonyl iridium hydride with 0.5 grams of tris(triphenylphosphine)carbonyl osmium hydride or 0.5 gram of tris(triphenylphosphine)carbonyl platinum hydride.

EXAMPLE 5

A rhodium complex with tri(n-butyl)phosphine is prepared by introducing 0.5 gram rhodium trichloride in 20 milliliters of water and 180 milliliters of methanol into a flask fitted with a reflux condenser. Carbon monoxide is bubbled into the liquid and then 10 milliliters of tri(n-butyl)phosphine is added and the flask contents are heated to and maintained at reflux for 45 minutes. To the flask is then added 5.0 milliliters hydrazine, the flask contents are cooled and transferred to a rotary evaporator and evaporated at 0.2 millimeters mercury pressure. The liquid residue is extracted with normal pentane and the extract is again evaporated.

The residue is dissolved in pentane placed in the flask with 100 milliliters methanol, carbon monoxide is bubbled through the flask while the contents are warmed to reflux and then 1.0 gram sodium borohydride and 50 milliliters each of methanol and water are added. The flask contents are cooled and evaporated to 10 milliliters of residue containing the rhodium complex with carbon monoxide and the tri(n-butyl)phosphine.

The hydroformylation is practiced by charging 5 milliliters of the residue, 2.0 grams tri(n-butyl)phosphine, 500 milliliters toluene and 117 grams propylene to the autoclave. The autoclave is pressured with 300 psi carbon monoxide and 300 psi of hydrogen, heated to 95° C. and maintained at that temperature for 20 minutes while a 45 psi drop in pressure ocurs. The autoclave is then heated to 150° C. and a 200 psi drop in pressure occurs. The autoclave is cooled, vented and recharged with 124 grams propylene and the same amounts of carbon monoxide and hydrogen. A 50 psi pressure drop is observed in 20 minutes at 95° C. and the autoclave is cooled, vented opened and the liquid contents weighed to determine an 80 gram weight increase. The products analyzed by gas chromatography are butyraldehydes with a normal to iso ratio of 1.8 to 1.0.

The preceding examples are intended solely to illustrate the mode of practicing the invention and to demonstrate the results obtainable thereby. It is not intended that this illustration be construed as unduly limiting of the invention but rather it is intended that the invention be defined by the method steps, conditions and reagents and their obvious equivalents set forth in the following claims:

I claim:

1. In a process for hydroformylating acyclic olefins having 2 to about 8 carbon atoms to form aldehydes, wherein the process is carried out in a reaction zone: (1) in the presence of a liquid reaction medium containing an inert organic solvent, (2) with carbon monoxide and hydrogen, (3) at a temperature of about 50° to about 200° C., and (4) at a pressure of about 1 to about 10,000 atmospheres, the improvement comprising:

charging to the reaction zone a catalyst consisting essentially of a complex combination of rhodium hydride with carbon monoxide and an organic ligand of the formula, wherein R is aryl of 6 to 8 carbon atoms.

2. The process of claim 1 wherein R is phenyl.
3. The process of claim 2 wherein the olefin is propylene.
4. The process of claim 2 wherein the olefin is ethylene.

* * * * *